United States Patent
Radice

(10) Patent No.: US 11,867,692 B2
(45) Date of Patent: Jan. 9, 2024

(54) COLORIMETRIC SENSOR FOR DETECTING BACTERIA AND/OR VIRUSES

(71) Applicant: DG Group S.P.A., Novara (IT)

(72) Inventor: Dino Radice, Milan (IT)

(73) Assignee: DG GROUP S.P.A., Novara (IT)

( * ) Notice: Subject to any disclaimer, the term of this patent is extended or adjusted under 35 U.S.C. 154(b) by 334 days.

(21) Appl. No.: 17/240,497

(22) Filed: Apr. 26, 2021

(65) Prior Publication Data

US 2021/0341464 A1 Nov. 4, 2021

(30) Foreign Application Priority Data

May 4, 2020 (IT) ........................ 102020000009727

(51) Int. Cl.
| | | |
|---|---|---|
| *G01N 33/68* | (2006.01) | |
| *G01N 21/33* | (2006.01) | |
| *G01N 21/64* | (2006.01) | |
| *G01N 33/52* | (2006.01) | |
| *C07C 309/65* | (2006.01) | |

(Continued)

(52) U.S. Cl.
CPC ......... *G01N 33/521* (2013.01); *G01N 33/532* (2013.01); *G01N 33/56911* (2013.01)

(58) Field of Classification Search
CPC ............... G01N 33/521; G01N 33/532; G01N 33/56911; G01N 21/78; G01N 33/56983; G01N 21/553; G01N 21/00; G01N 33/52; G01N 21/255; G01N 2021/258;

(Continued)

(56) References Cited

U.S. PATENT DOCUMENTS

| | | | |
|---|---|---|---|
| 2004/0132217 A1* | 7/2004 | Prince .................. | G01N 33/521 436/518 |
| 2013/0065777 A1 | 3/2013 | Altug et al. | |
| 2019/0266169 A1 | 8/2019 | Ho | |

FOREIGN PATENT DOCUMENTS

WO WO-2020260716 A2 * 12/2020 ....... G01N 33/54306

OTHER PUBLICATIONS

Paternò, Giuseppe M., et al. "Integration of bio-responsive silver in 1D photonic crystals: Towards the colorimetric detection of bacteria." Faraday Discussions 223 (2020): 125-135. (Year: 2020).*

(Continued)

*Primary Examiner* — Jennifer Wecker
*Assistant Examiner* — Oyeleye Alexander Alabi
(74) *Attorney, Agent, or Firm* — Mark Malek; Jonathan Staudt; Widerman Malek, PL

(57) ABSTRACT

A colorimetric sensor for detecting bacteria and/or viruses includes one or more layers having a photonic crystal structure, a functional layer comprising a nanomaterial capable of generating bacteria- and/or viruses-bioresponsive surface plasmon overlapping the one or more layers having the photonic crystal structure. The bacteria- and/or viruses-bioresponsive nanomaterial of the functional layer is doped with proteinic substances or antibodies acting as virus receptors, or the colorimetric sensor comprises a receptor layer comprising proteinic substances or antibodies acting as virus receptors. The functional layer and receptor layer overlap each other. Alternatively, or in addition to, the colorimetric sensor comprises a plasmonic nanostructured layer comprising nanostructures such to generate plasmonic colors, overlapping the one or more layers having the photonic crystal structure.

21 Claims, 14 Drawing Sheets

(51) Int. Cl.
  *C07C 309/73* (2006.01)
  *A01N 1/02* (2006.01)
  *G01N 1/40* (2006.01)
  *G01N 33/543* (2006.01)
  *G01N 33/532* (2006.01)
  *G01N 33/569* (2006.01)

(58) Field of Classification Search
  CPC ......... G01N 2021/7769; G01N 21/554; G01N 2333/165; G02B 1/005
  See application file for complete search history.

(56) References Cited

OTHER PUBLICATIONS

Giuseppe M. Paterno et al., "Integration of bio-responsive silver in aD photonic crystals: towards the colorimetric detection of bacteria", Faraday Discussions, vol. 223, Mar. 6, 2020, pp. 125-136.
Italian Search Report dated Jan. 18, 2021; 107 pages.

* cited by examiner

COLORIMETRIC SENSOR FOR DETECTING BACTERIA AND/OR VIRUSES

RELATED APPLICATIONS

This is a utility patent application which claims the benefit of IT 102020000009727, filed on May 4, 2020, the contents of which are hereby incorporated by reference in its entirety.

TECHNICAL FIELD OF THE INVENTION

The present invention refers to a calorimetric sensor for detecting bacteria and/or viruses.

PRIOR ART

Colorimetric sensors for detecting bacterial contaminant agents, such as *Escherichia coli* bacteria, are known.

An example of a colorimetric sensor for detecting bacteria, such as *Escherichia coli* bacteria, is described in G. M. Paterno, L. Moscardi, S. Donini, D. Ariodanti, I. Kriegel, M. Zani, E. Parisini, F. Scotognella, G. Laznani, "Hybrid One-Dimensional Plasmonic Photonic Crystals for Optical Detection of Bacteria Contaminants", J. Phys. Chem. Lett. 2019, 10, 4980-4986. Such sensor comprises a silver layer (plasmonic metal) and a one-dimensional photonic crystal. Silver features a bioresponsivity to the *Escherichia coli* bacteria which modifies the photonic response when comes in contact with this latter. In other words, if the presence of bacteria is detected, for example by putting in contact the secretions of a subject with the silver layer, a sensor color change is perceived.

However, in order to detect other contaminant agents or also viruses, generally having much smaller size than those of the bacteria, a greater sensibility of the sensor is required.

BRIEF SUMMARY OF THE INVENTION

Therefore, it is an object of the present invention to provide a colorimetric sensor having an improved sensibility, which enables to accurately detect bacteria and also viruses, such as COVID-19 virus.

This and other objects are met by a colorimetric sensor for detecting bacteria and/or viruses according to claim 1 and by a colorimetric sensor for detecting bacteria and/or viruses according to claim 18.

Dependent claims define possible advantageous embodiments of the invention.

BRIEF DESCRIPTION OF THE DRAWINGS

In order to better understand the invention and appreciate the advantages thereof, some exemplifying non-limiting embodiments thereof will be described in the following with reference to the attached figures, wherein.

Figure 1:
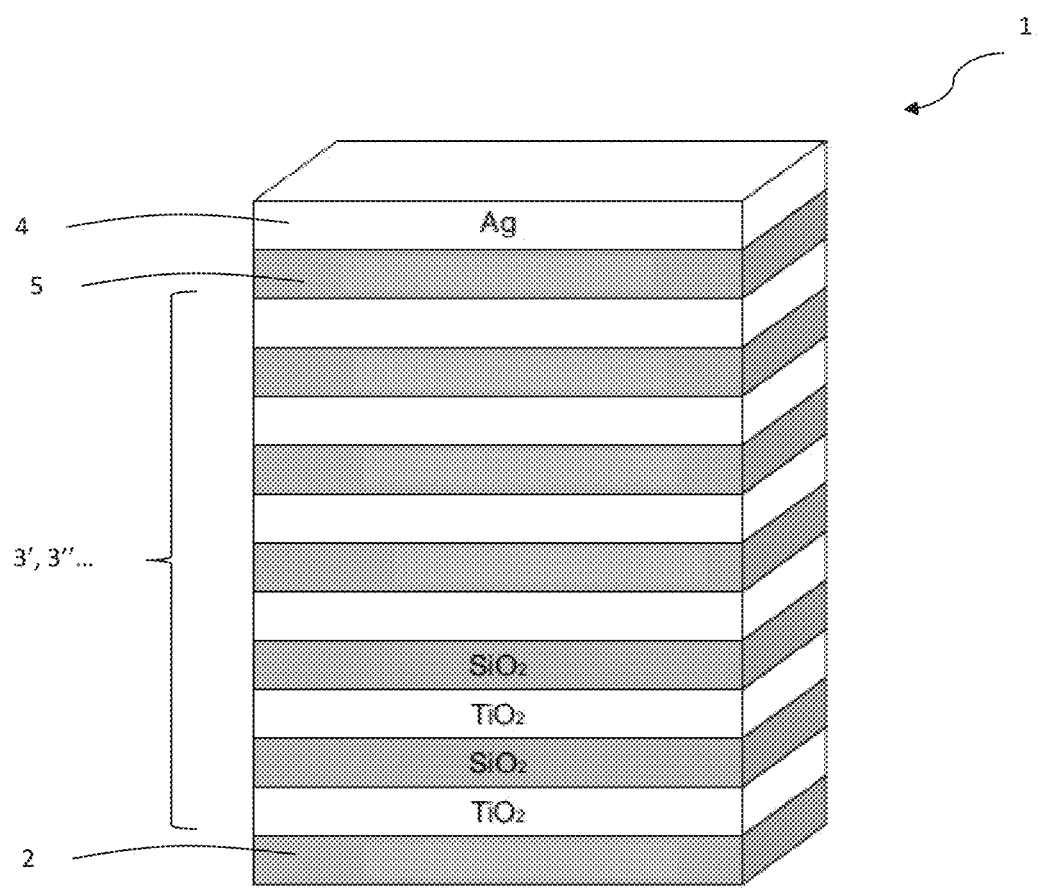
FIG. 1 is a cross-section schematic view of a colorimetric sensor according to a first possible embodiment of the invention.

Figures from 8a to 8c are perspective views, in different conditions of use, of a kit comprising the calorimetric sensor according to a possible embodiment of the invention;

Figures from 9a to 9c are perspective views, in different conditions of use, of a kit comprising the colorimetric sensor according to a further possible embodiment of the invention;

Figures from 10a to 10c are perspective views, in different conditions of use, of a kit comprising the calorimetric sensor according to a further possible embodiment of the invention;

FIGS. 11-14 are cross-section schematic views of a colorimetric sensor according to further possible embodiments of the invention.

With reference to the attached figures from 1 to 6, a calorimetric sensor for detecting bacteria and/or viruses is generally shown by reference 1. Sensor 1 can be made for example as a label applied to one or more sheets or on a roll-shaped support or, for example, applied on an instrument 200 as is illustrated in Figures from 8 to 10, for example. By way of illustration, directly or indirectly by a withdrawing device 201 of the instrument 200, the sensor 1, embodied by a label, can be dipped in a container receiving a sample of secretions to be analyzed of a subject. Or directly or indirectly by the withdrawing device 201 of the instrument 200, the sensor 1, embodied by a label, can be applied for example on the tongue of the subject of which it is desired to check whether is infected.

For example, with reference to Figures from 8a to 8c, the instrument 200 can comprise a body shaped as a spatula 202 on which the sensor 1 is applied.

With reference to Figures from 9a to 9c, the instrument 200 can comprise a spatula-shaped body 202 on which the sensor 1 is applied and a second spatula-shaped body 203 on which the withdrawing device 201 is applied. The rotation of the second spatula body 203 with respect to the spatula body 202 causes the withdrawing device 201 to come in contact with the sensor 1. According to the illustrated embodiment, the relative rotation of the spatula bodies is about an axis perpendicular to the longitudinal axes of the spatula bodies which are aligned to each other.

With reference to Figures from 10a to 10c, the instrument 200 can comprise a spatula-shaped body 202 on which the sensor 1 is applied and a second spatula-shaped body 203 on which the withdrawing device 201 is applied. The rotation of the second spatula body 203 with respect to the spatula body 202 causes the withdrawing device 201 to come in contact with the sensor 1. According to the illustrated embodiment, the relative rotation of the spatula bodies is about an axis parallel to the longitudinal axes of the spatula bodies which are side-by-side and parallel to each other.

Preferably, the colorimetric sensor 1 comprises a support layer 2 having, according to a possible embodiment, the function of supporting further overlying layers. The support layer 2 can be made, in an exemplifying non-limiting way, of polycarbonate, or PVC, or Teslin, or polyester, or similar materials, or can be made of a paper material.

The colorimetric sensor 1 comprises one or more, preferably a plurality of layers 3', 3", . . . having a photonic crystal structure, preferably overlapping the support layer 2. In optics and microphotonics, the term "photonic crystal"

means a structure having a refraction index with a periodic modulation on scales comparable with the wavelength of the light or, more generally, of an electromagnetic radiation. Based on the type of the periodic modulation of the refraction index, the photonic crystals are classified in:
- one-dimensional photonic crystals, having a periodicity of the refraction index only in one direction (also known as Bragg mirrors);
- two-dimensional photonic crystals, having a periodicity of the refraction index in two directions;
- three-dimensional photonic crystals, having a periodicity of the refraction index in three directions.

Figure 7:
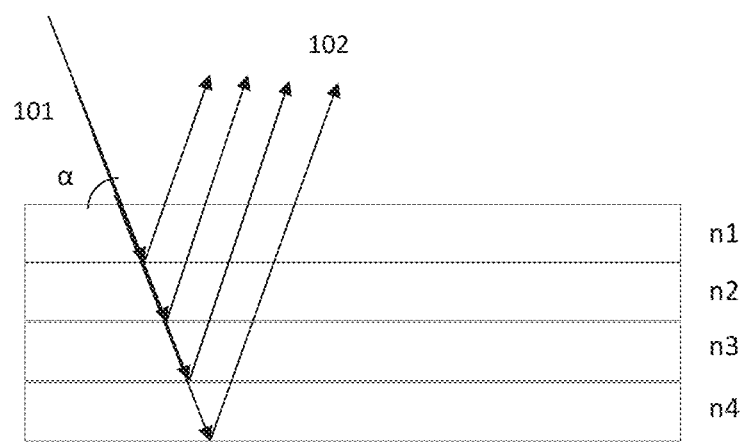
FIG. 7 is a cross-section schematic view of a one-dimensional photonic crystal.
Figure 8:
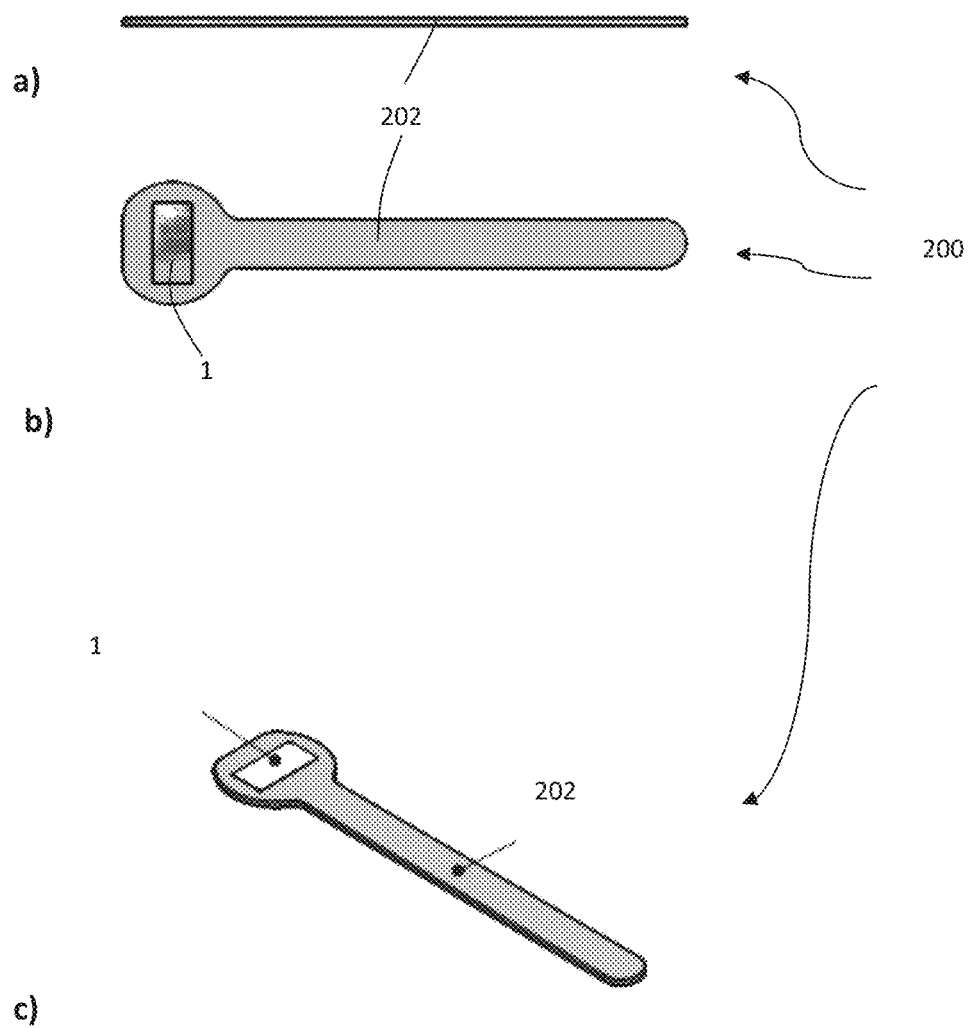
Figure 9:
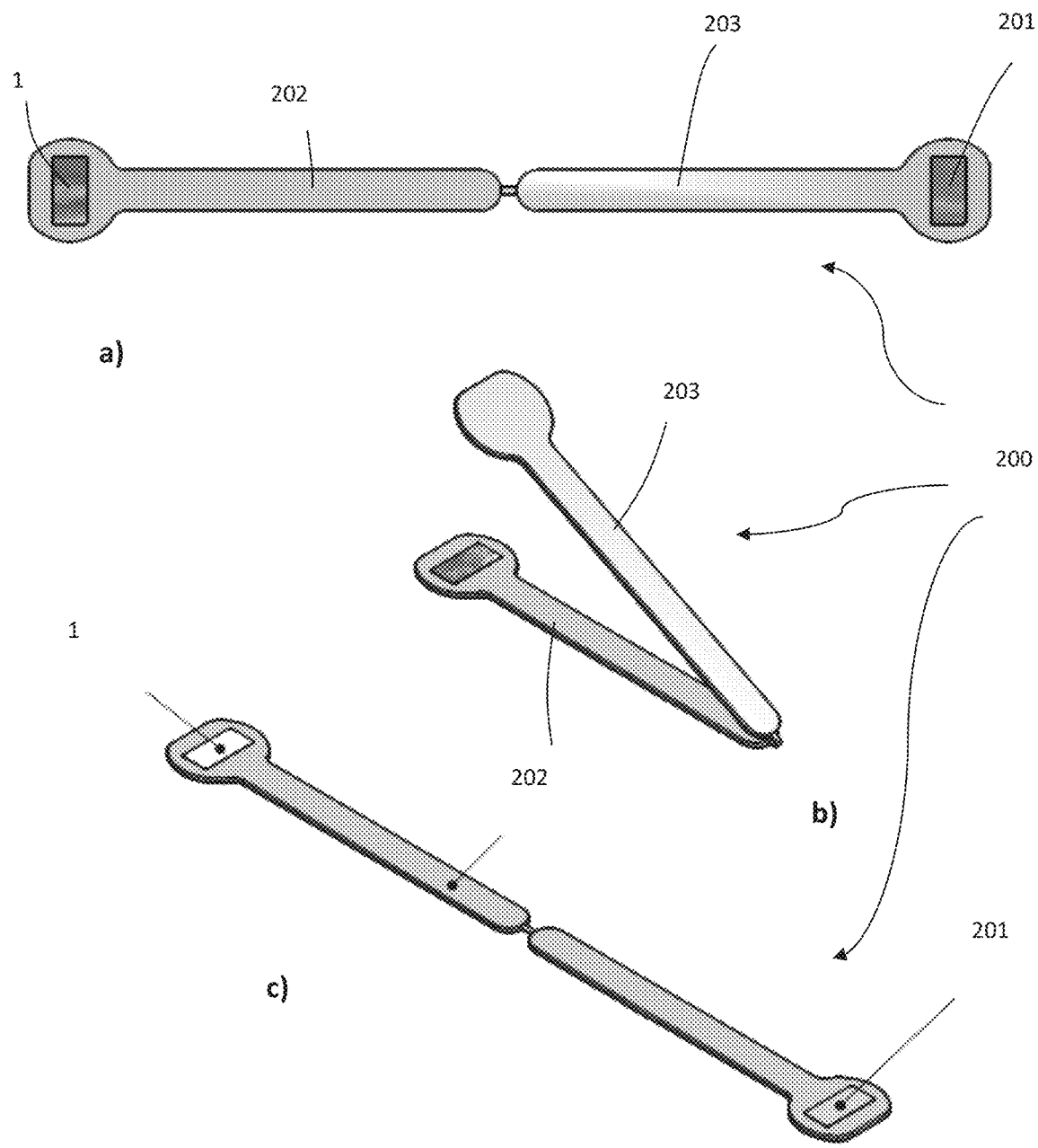
Figure 10:
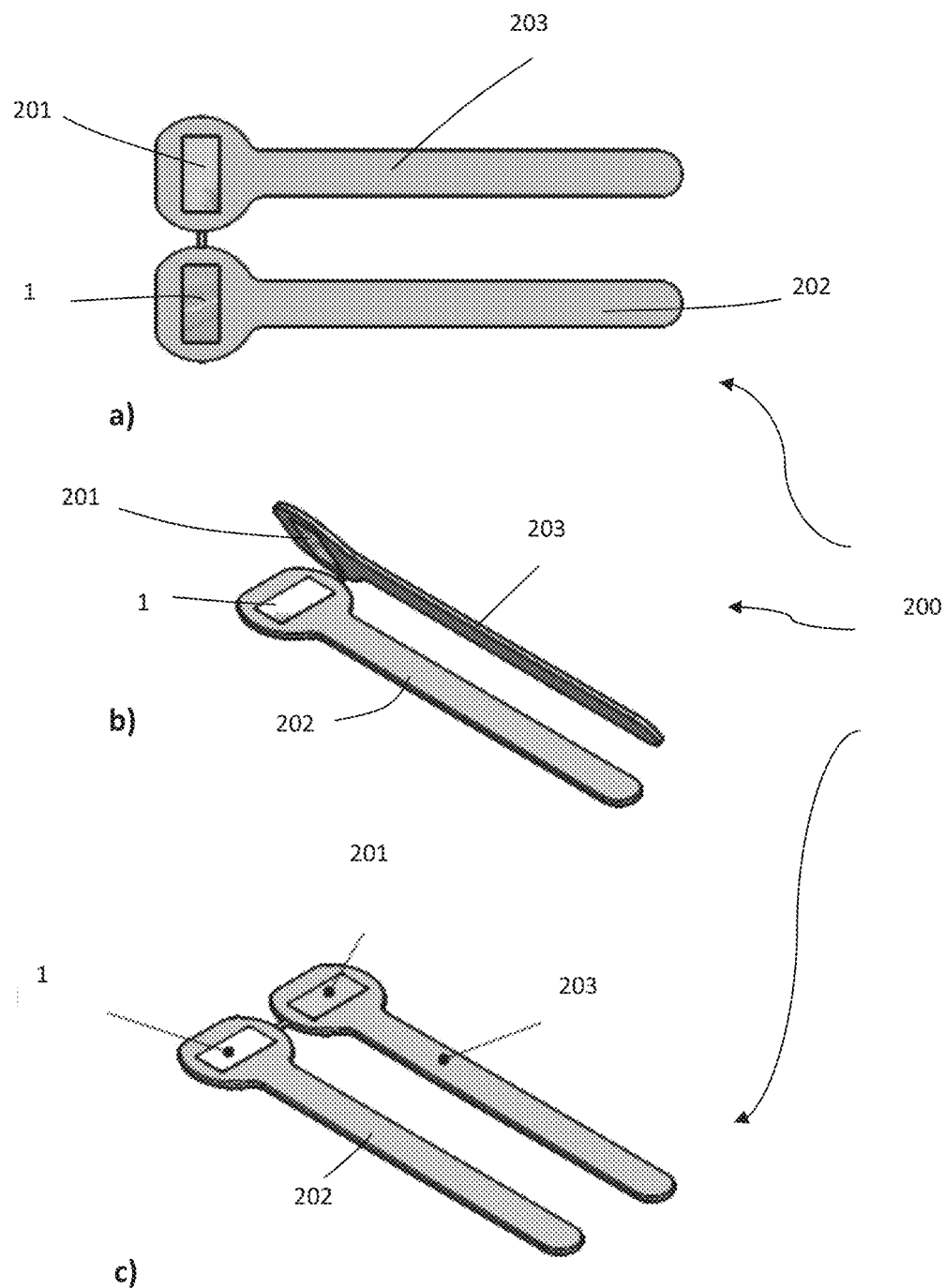

According to an embodiment, the layers with the photonic crystal structure 3, 3", . . . comprise a one-dimensional photonic crystal structure. With reference to FIG. 7, the one-dimensional photonic crystal structure comprises a plurality of layers having respective refraction indexes n1, n2, n3, n4. Given a light ray 101 incident by an incidence angle α, the overall reflected light is given by a beam 102 of reflected light rays. By suitably selecting the periodicity and refraction indexes of the layers, it is possible to manufacture mirrors having a very high reflection coefficient falling in a determined wavelength range. Consequently, changing the incidence angle α of the incident light ray 101, an observer, considered in a stationary position with respect to the photonic crystal structure, will observe a color change of the structure. Analogously, the observer will see color changes in the photonic crystal structure if, for the same incidence angle of the incident light ray, he/she changes his/her position and/or orientation with respect to the photonic crystal structure and consequently with respect to the reflected light beam 102.

According to an embodiment, the layers with the photonic crystal structure 3, 3" . . . comprise a plurality of alternated layers of silica ($SiO_2$) and titanium dioxide ($TiO_2$).

Moreover, the colorimetric sensor 1 comprises a functional layer 4 comprising a nanomaterial capable of generating, under determined conditions, an excitation of the surface electrons, in other words a surface plasmon, bioresponsive to bacteria and/or viruses, overlapping, directly or indirectly, the one or more layers with a crystal photonic structure 3', 3", . . . . In the present description and in the attached claims, the term "bioresponsive" means that the considered material, when comes in contact with and is stimulated by molecules of bacteria or viruses, modifies its characteristics, particularly modifies the plasmonic resonance energy, which depends on what is placed in the interface between the material and bacterium/virus. Therefore, any element which is made to bond to the surface of a nanoparticle of a nanomaterial, will contribute to change the plasmon energies, so that colors different from the ones of the macroscopic material will be observed.

For example, the antibacterial properties of silver, which modifies its electrostatic surface characteristics by bonding to a bacterial membrane, are known. Moreover, recent studies have shown how colloidal silver and gold are bioresponsive to some viruses.

According to an embodiment, the nanomaterial of the functional layer 4 comprises silver, or a silver-based material (such as colloidal silver), or gold, or a gold-based material. Obviously, further nanomaterials not explicitly mentioned, which are not plasmonic and bioresponsive to particular viruses or bacteria, can be provided.

Preferably, the functional layer 4 features a nanometric thickness, in other words in the nanometer range. According to a possible embodiment, the functional layer 4 has a thickness comprised between 4 and 20 nanometers. This very thin layer can be for example applied by different deposition techniques: vacuum deposition, sputtering, physical vapor deposition, or other spraying techniques.

In other words, if bacteria are detected, for example by bringing in contact secretions of a subject infected by the bacteria with the functional layer 4, the structure change of this latter, as hereinbefore described, in the nanomaterial parts in contact with the bacteria themselves, due to its bioresponsivity, causes the plasmon energies to change, showing in this part colors different from the ones of the macroscopic material. Such color change is amplified by the overall interferential electro-optical structure of the photonic crystal 3', 3", layers of the sensor 1.

According to an embodiment, the functional layer 4 is selectively deposed so to form for example an alphanumeric string, an image, a symbol, a code. For example, the functional layer 4 can be deposed such that one or more writings indicating the bacteria or the virus to be identified (e.g. COVID-19) are visible.

Then, it is known that some protein substances or antibodies act as virus receptors. For example, it was observed, in case of COVID-19 and SARS-CoV, the ACE2 protein (angiotensin-converting system 2) acts as a membrane receptor. The Applicant has surprisingly found that adding such proteins or antibodies to the functional layer 4 enables the sensor 1 to detect also viruses, such as COVID-19 viruses, present for example in secretions of people or other subjects or liquids, and contributes to modify the plasmon energies causing, also in this case, an interferential electro-optical change of the sensor structure including the layers of the photonic crystal structure 3, 3" . . . , which in turn causes an optically perceived color change.

To this purpose, the bioresponsive plasmonic nanomaterial, forming the functional layer 4, can be doped with the above-cited protein substances or antibodies acting as virus receptors. Alternatively, the sensor 1 can comprise a receptor layer 5 comprising the above-cited protein substances or antibodies acting as virus receptors, wherein the functional layer 4 and receptor layer 5 overlap each other, preferably in contact with each other. Also the receptor layer 5 preferably features a nanometric thickness. According to an embodiment, the sensor 1 further comprises a second functional layer 6, preferably comprising the same nanomaterial as the one of the functional layer 4, overlapping the receptor layer 5, Moreover, the second functional layer 6 preferably features a nanometric thickness, still more preferably comprised between 4 and 20 nanometers.

As an alternative or in addition to what was hereinbefore discussed, in order to improve the sensibility of sensor 1 so that the same is capable to better detect bacteria and also the presence of viruses, which generally have much smaller dimensions than the ones of the bacteria, the sensor 1 can comprise a plasmonic nanostructured layer 7, overlapping the layers having a photonic crystal structure 3, 3", . . . , comprising nanostructures capable of forming plasmonic colors.

The plasmonic nanostructured layer 7 is a nanoetched structure, in other words comprising etched nanostructures which are shaped in order to increase the strength of an electromagnetic field generated by photonic and plasmonic resonances intrinsic to the nanostructures, increasing in turn the interaction between light and matter, in order to obtain the so-called plasmonic colors, known also as structural colors. Such plasmonic colors are obtained by a resonance interaction between the light and nanostructures of the plasmonic nanostructured layer 7 ("nanostructured grating"), etched in a metal layer or in a polymeric layer coated by metal nanoparticles. Surface localized plasmons generated by these nanostructures enable, by nanometrically controlling their morphology, to generate polarized colors without pigments. The nanostructures can be made by the electron-beam technique, for example.

The nanostructures of the plasmonic nanostructured layer 7 enable to cause the surface plasmonic resonance phenomenon. Consequently, the nanostructures of the plasmonic nanostructured layer 7 enable to improve the sensor 1 sensibility, in other words to intensify the phenomenon of the sensor color change, hereinbefore described, if the presence of a bacterial agent, or particularly of a virus, such as COVID-19, is detected.

According to an embodiment, the nanostructures of the plasmonic nanostructured layer 7 have a zero-diffraction order, in other words are capable to only produce reflection and refraction, and not a diffraction, of incident light waves.

According to an embodiment, the nanostructures of the plasmonic nanostructured layer 7 are configured to produce a polarized light optical effect.

With reference to the attached figures from 1 to 6, possible alternative embodiments of the invention will be herein described First Embodiment (FIG. 1)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the receptor layer 5;
the functional layer 4, for example of silver, Ag.

Figure 2:
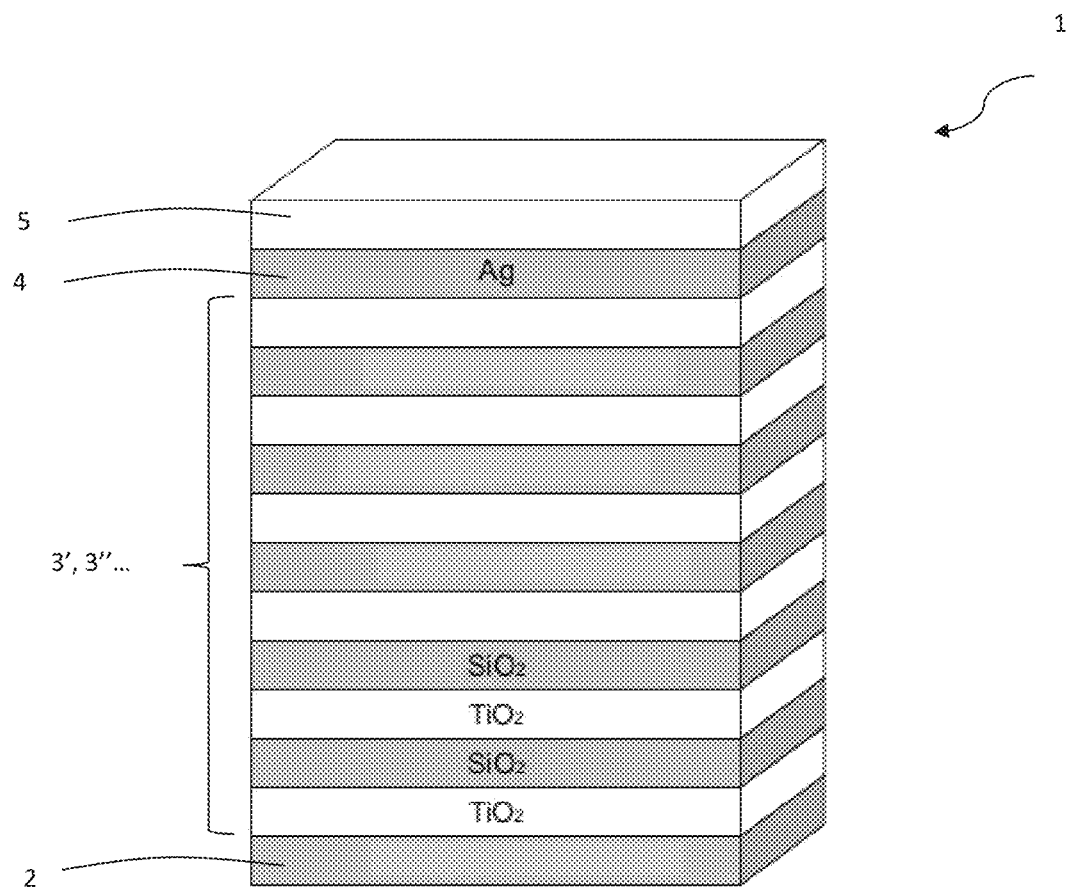
FIG. 2 is a cross-section schematic view of a calorimetric sensor according to a second possible embodiment of the invention.

Second Embodiment (FIG. 2)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the functional layer 4, for example made of silver, Ag;
the receptor layer 5.

Figure 3:
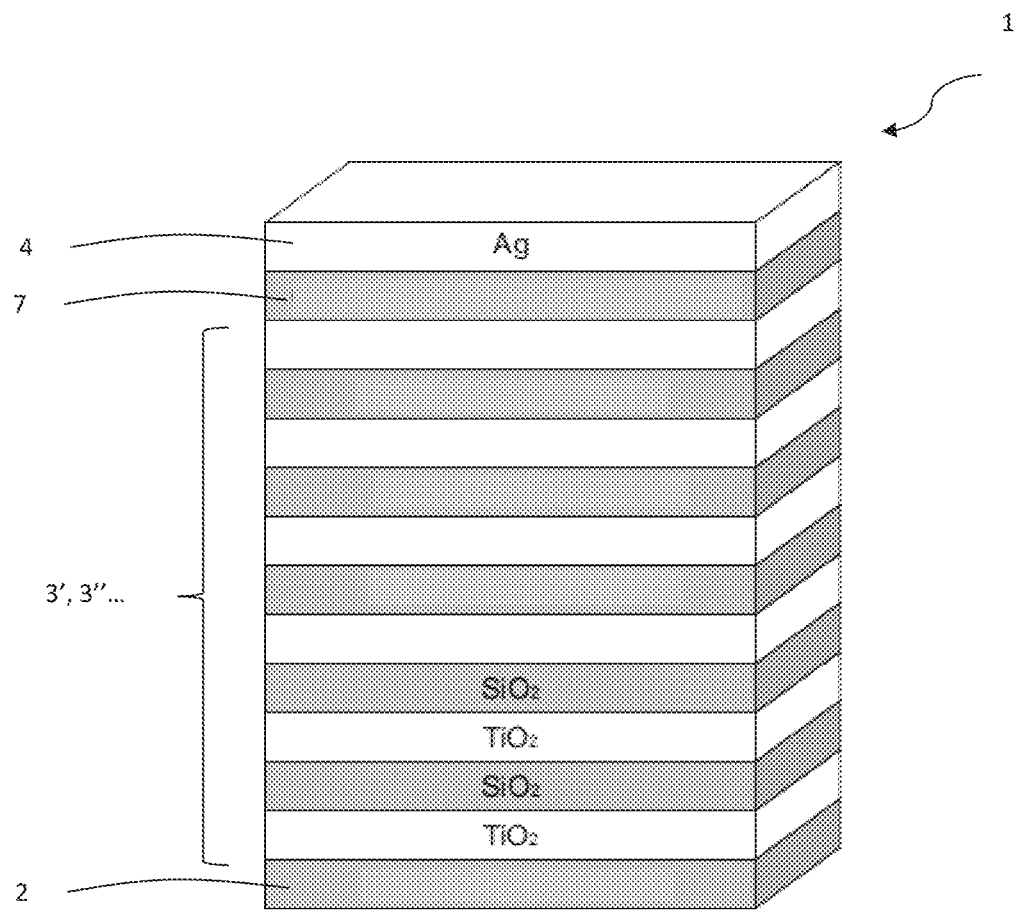
FIG. 3 is a cross-section schematic view of a colorimetric sensor according to a third possible embodiment of the invention.

Third Embodiment (FIG. 3)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the plasmonic nanostructured layer 7;
the functional layer 4, for example made of silver, Ag.

Figure 4:
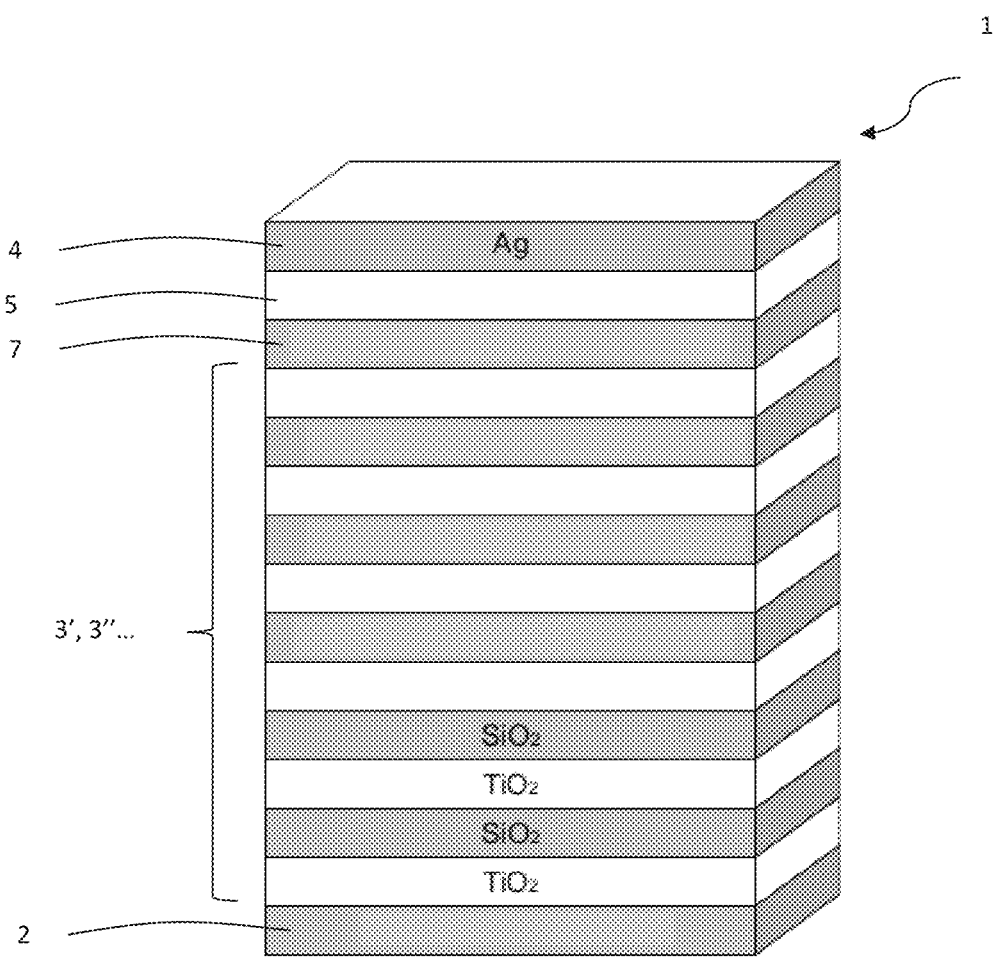
FIG. 4 is a cross-section schematic view of a colorimetric sensor according to a fourth possible embodiment of the invention.

Fourth Embodiment (FIG. 4)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the plasmonic nanostructured layer 7;
the receptor layer 5;
the functional layer 4, for example made of silver, Ag.

Figure 5:
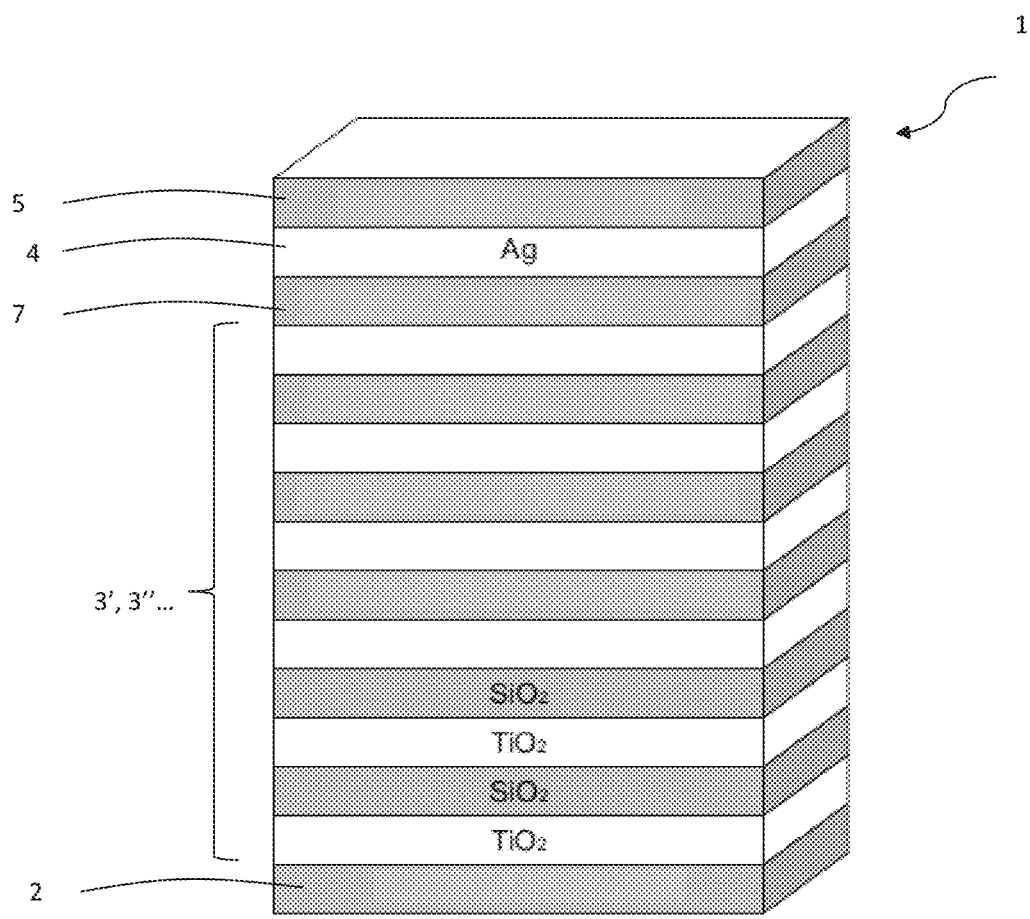
FIG. 5 is a cross-section schematic view of a calorimetric sensor according to a fifth possible embodiment of the invention.

Fifth Embodiment (FIG. 5)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the plasmonic nanostructured layer 7;
the functional layer 4, for example of silver, Ag;
the receptor layer 5.

Figure 6:
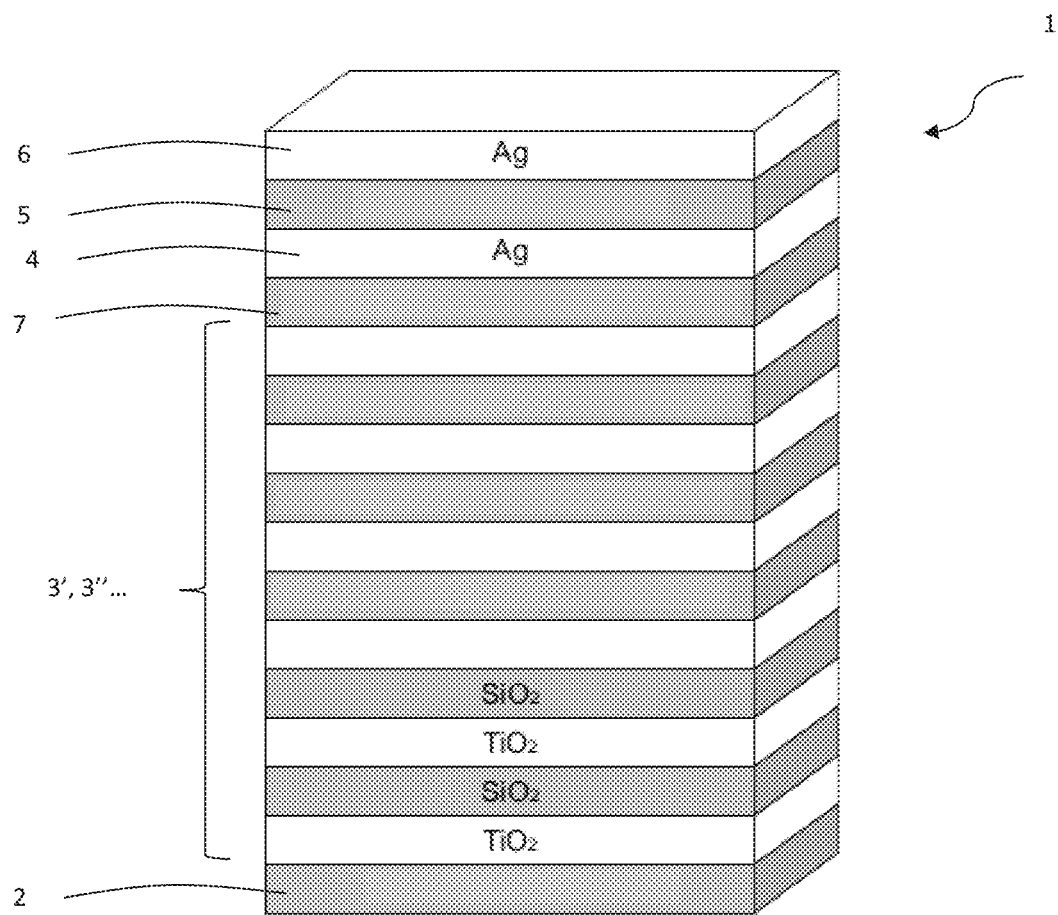
FIG. 6 is a cross-section schematic view of a colorimetric sensor according to a sixth possible embodiment of the invention.

Sixth Embodiment (FIG. 6)

According to this embodiment, the colorimetric sensor 1 comprises sequentially (from the bottom to the top with reference to the orientation of the figure):
the support layer 2;
the plurality of layers having a structure of alternated photonic crystals 3', 3", . . . for example of $SiO_2$ and $TiO_2$;
the plasmonic nanostructured layer 7;
the functional layer 4, for example of silver, Ag;
the receptor layer 5;
the second functional layer 6, for example of silver.

It is observed that, in the above-described embodiments, the receptor layer 5, if provided, can be alternatively substituted by doping the functional layer 4 and/or the second functional layer 6.

Moreover, it is observed that, in the present description and the attached claims, the term "overlapped", with reference to the sensor 1 layers, does not necessarily also imply a direct contact between the cited overlapped layers. Therefore, such layers could be directly in contact with each other, or, alternatively, they could have one or more intermediate layers arranged between them, provided that they still overlap. Further, the term "overlap" does not imply any order of the layers indicated as overlapping each other.

According to another variant of the present invention, the colorimetric sensor 1 can be devoid of the layers 3', 3", . . . having a photonic crystal structure if it comprises the plasmonic nanostructured layer 7. Indeed, it was observed that the presence the plasmonic nanostructured layer 7 is sufficient to ensure a suitable sensibility even in absence of the layers 3', 3", . . . having a photonic crystal structure. For example, all the variants shown in the FIGS. 3-6 can be embodied without the layers where all the other shown layers are maintained (FIGS. 11-14).

Figure 11:
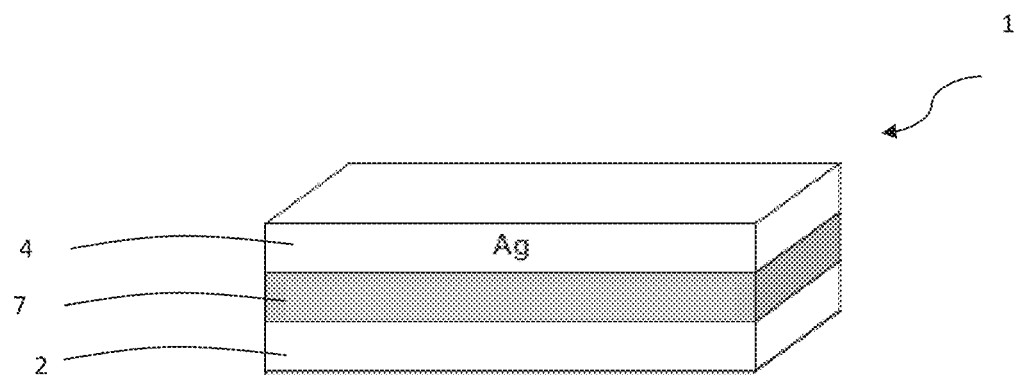

Seventh Embodiment (FIG. 11)

According to this embodiment, the colorimetric sensor 1 comprises sequentially (from the bottom to the top with reference to the orientation of the figure):
the support layer 2;
the plasmonic nanostructured layer 7;
the functional layer 4, for example made of silver, Ag.

Figure 12:
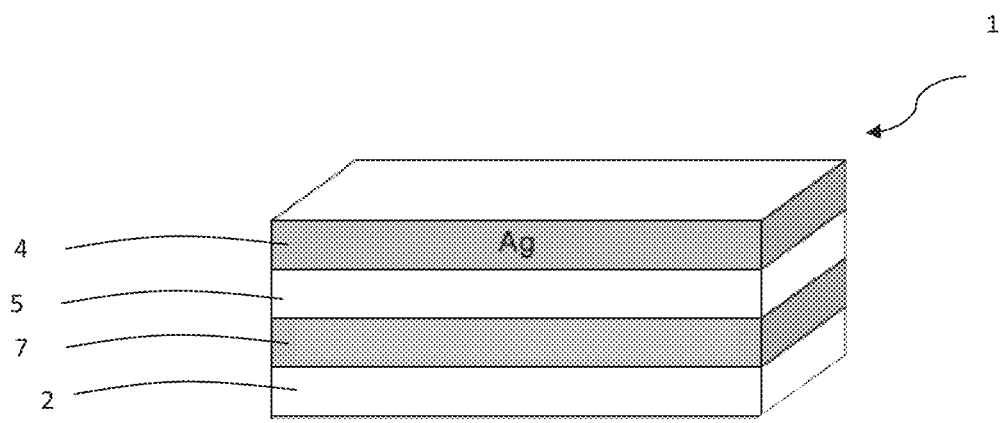

Eighth Embodiment (FIG. 12)

According to this embodiment, the colorimetric sensor 1 comprises sequentially (from the bottom to the top with reference to the orientation of the figure):
the support layer 2;
the plasmonic nanostructured layer 7;
the receptor layer 5;
the functional layer 4, for example made of silver, Ag.

Figure 13:
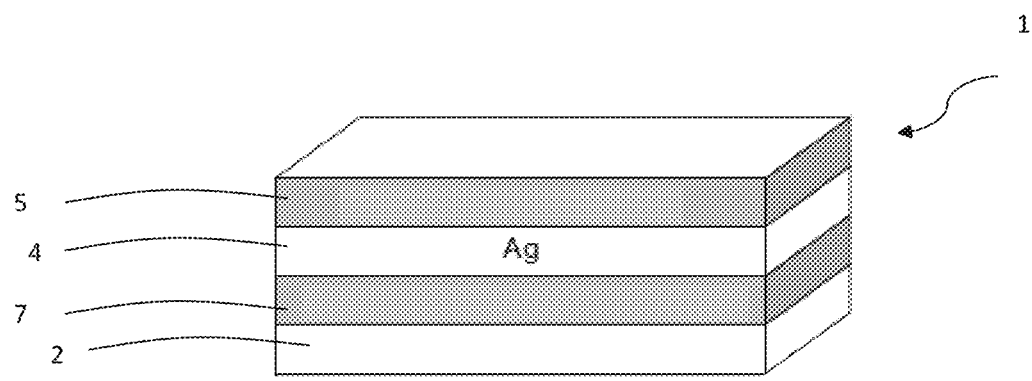

Ninth Embodiment (FIG. 13)

According to this embodiment, the colorimetric sensor 1 comprises sequentially (from the bottom to the top with reference to the orientation of the figure):
the support layer 2;
the plasmonic nanostructured layer 7;
the functional layer 4, for example of silver, Ag;
the receptor layer 5.

Figure 14:
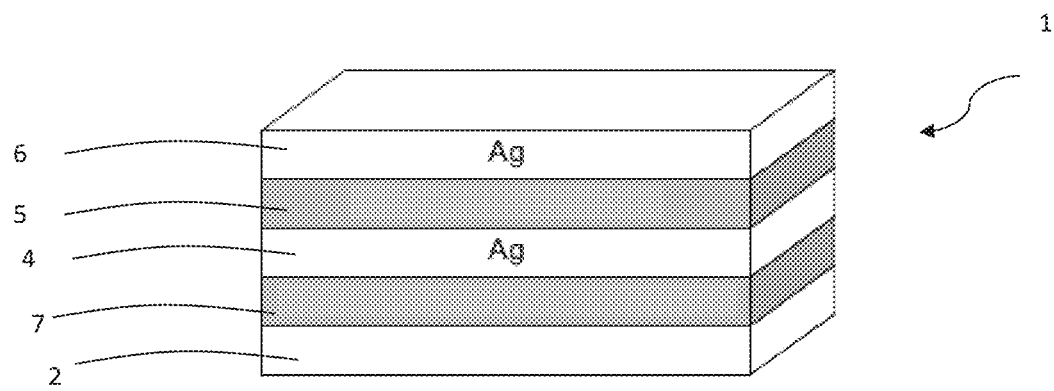

Tenth Embodiment (FIG. 14)

According to this embodiment, the colorimetric sensor 1 comprises sequentially (from the bottom to the top with reference to the orientation of the figure):
the support layer 2;
the plasmonic nanostructured layer 7; the functional layer 4, for example of silver, Ag;
the receptor layer 5;
the second functional layer 6, for example of silver.

It is observed that, even in the above-described embodiments, the receptor layer 5, if provided, can be alternatively substituted by doping the functional layer 4 and/or the second functional layer 6.

A person skilled in the art in order to satisfy specific contingent needs could introduce many additions, modifications, or substitutions of elements with other operatively equivalent ones to the above given description of the colorimetric sensor without falling out of the scope of the attached claims.

The invention claimed is:

1. A colorimetric sensor for detecting bacteria and/or viruses, comprising:
a plurality of layers having a photonic crystal structure;
a functional layer comprising a nanomaterial capable of generating a surface plasmon, bacteria- and/or viruses-bioresponsive, overlapping the plurality of layers having the photonic crystal structure; and
a receptor layer comprising proteinic substances or antibodies, the receptor layer being configured to act as a virus receptor;
wherein the functional layer and the receptor layer are overlapped and in direct contact with each other.

2. The colorimetric sensor according to claim 1, wherein said plurality of layers with a photonic crystal structure comprise a one-dimensional photonic crystal structure.

3. The colorimetric sensor according to claim 1, wherein said plurality of layers having the photonic crystal structure comprise a plurality of alternated layers of silica ($SiO_2$) and titanium dioxide ($TiO_2$).

4. The colorimetric sensor according to claim 1, wherein the nanomaterial of said functional layer comprises silver or a silver-based material, or gold, or a gold-based material.

5. The colorimetric sensor according to claim 1, wherein said functional layer has a thickness between 4 and 20 nanometers.

6. The colorimetric sensor according to claim 1, wherein said proteinic substances or antibodies acting as virus receptors comprise ACE2 protein (angiotensin-converting enzyme 2).

7. The colorimetric sensor according to claim 1, further comprising a second functional layer comprising a nanomaterial capable of generating a surface plasmon, bacteria- and/or viruses-bioresponsive, overlapping the receptor layer and opposite to the functional layer.

8. The colorimetric sensor according to claim 7, wherein said second functional layer comprises the same nanomaterial as the functional layer.

9. The colorimetric sensor according to claim 7, wherein said second functional layer and said receptor layer are directly in contact with each other.

10. The colorimetric sensor according to claim 7, wherein said second functional layer has a thickness between 4 and 20 nanometers.

11. The colorimetric sensor according to claim 1, further comprising a supporting layer, wherein said plurality layers having the photonic crystal structure overlap the supporting layer.

12. The colorimetric sensor according to claim 1 wherein the colorimetric sensor is conformed as a label.

13. The Colorimetric sensor according to claim 1 wherein the colorimetric sensor is applied to an instrument, to sheets or a roll-shaped support.

14. The colorimetric sensor according to claim 1, wherein the functional layer is selectively deposed so as to form an alphanumeric string, an image, a symbol, or a code.

15. A colorimetric sensor for detecting bacteria and/or viruses comprising:
a functional layer comprising a nanomaterial capable of generating a surface plasmon, bacteria- and/or viruses-bioresponsive;
wherein the bacteria- and/or viruses-bioresponsive nanomaterial of the functional layer comprises at least one of proteinic substances and antibodies, the functional layer being configured to act as a virus receptor, or the colorimetric sensor comprises a receptor layer comprising at least one of proteinic substances and antibodies, the receptor layer being configured to act as a virus receptor;
wherein the functional layer and the receptor layer are overlapped and in direct contact with each other; and
wherein the colorimetric sensor further comprises a plasmonic nanostructured grating comprising etched nanostructures such to generate plasmonic colors.

16. The colorimetric sensor according to claim 15 wherein the nanomaterial of said functional layer comprises silver or a silver-based material, or gold, or a gold-based material.

17. The colorimetric sensor according to claim 1 wherein the colorimetric sensor comprises a plasmonic nanostructured layer comprising etched nanostructures such to generate plasmonic colors, overlapping the plurality of layers having the photonic crystal structure.

18. A colorimetric sensor for detecting bacteria and/or viruses comprising:
- a functional layer comprising a nanomaterial capable of generating a surface plasmon, bacteria- and/or viruses-bioresponsive; and
- a receptor layer comprising at least one of proteinic substances and antibodies, the receptor layer being configured to act as a virus receptor;
- wherein the colorimetric sensor further comprises a plasmonic nanostructured grating comprising etched nanostructures such to generate plasmonic colors.

19. The colorimetric sensor according to claim 17, wherein said etched nanostructures of the plasmonic nanostructured layer are shaped in order to cause a surface plasmonic resonance.

20. The colorimetric sensor according to claim 17, wherein the diffraction order of said etched nanostructures of the nanostructured plasmonic layer is zero.

21. The colorimetric sensor according to claim 17, wherein said etched nanostructures of the nanostructured plasmonic layer are configured for causing a polarized light optical effect.

* * * * *